United States Patent [19]

Merger et al.

[11] Patent Number: 5,268,499

[45] Date of Patent: Dec. 7, 1993

[54] PREPARATION OF MIXTURES OF 3-AMINOPROPIONITRILE AND ETHYLENE CYANOHYDRIN

[75] Inventors: Franz Merger, Frankenthal; Martin Brudermueller, Mannheim; Wolfgang Harder, Weinheim; Juergen Hartig, Gruenstadt; Dieter Franz, Ludwigshafen, all of Fed. Rep. of Germany

[73] Assignee: BASF Aktiengesellschaft, Ludwigshafen, Fed. Rep. of Germany

[21] Appl. No.: 47,303

[22] Filed: Apr. 19, 1993

[30] Foreign Application Priority Data

Apr. 25, 1992 [DE] Fed. Rep. of Germany ....... 4213749

[51] Int. Cl.$^5$ .......................................... C07C 253/30
[52] U.S. Cl. .................... 558/451; 558/452; 558/459
[58] Field of Search .................... 558/452, 451, 459

[56] References Cited

U.S. PATENT DOCUMENTS

| | | | |
|---|---|---|---|
| 1,992,615 | 2/1935 | Hoffmann et al. | 260/464 |
| 2,019,903 | 11/1935 | Heitmann | 154/30 |
| 2,401,429 | 6/1946 | Kung | 260/464 |
| 2,448,013 | 8/1948 | Buc et al. | 260/465.5 |
| 2,653,162 | 9/1953 | Luskin | 260/465.6 |
| 2,816,136 | 12/1967 | Selcer et al. | 260/465.6 |
| 3,914,280 | 10/1975 | Yamakami et al. | 260/465.5 A |
| 3,935,256 | 1/1976 | Verbeeck et al. | 260/534 A |
| 4,319,024 | 3/1982 | Peeters et al. | 558/451 X |
| 4,709,072 | 11/1987 | Mercer et al. | 558/451 X |
| 4,965,362 | 10/1990 | Mercer et al. | 558/451 X |
| 5,196,589 | 3/1993 | O'Lenich, Jr. et al. | 558/452 X |

FOREIGN PATENT DOCUMENTS

| | | |
|---|---|---|
| 352504 | 1/1990 | European Pat. Off. . |
| 598185 | 9/1931 | Fed. Rep. of Germany . |
| 1189975 | 4/1965 | Fed. Rep. of Germany . |
| 2436651 | 2/1975 | Fed. Rep. of Germany . |
| 3522906 | 1/1987 | Fed. Rep. of Germany . |
| 1007690 | 10/1965 | United Kingdom . |

*Primary Examiner*—Joseph Paul Brust
*Attorney, Agent, or Firm*—Keil & Weinkauf

[57] ABSTRACT

A process for preparing mixtures of 3-aminopropionitrile of the formula I $$H_2N-CH_2-CH_2-CN \qquad (I)$$

and ethylene cyanohydrin of the formula II $$HO-CH_2-CH_2-CN \qquad (II)$$

comprises reacting bis (2-cyanoethyl) ether of the formula III $$NC-CH_2-CH_2-O-CH_2-CH_2-CN \qquad (III)$$

with ammonia at from 50 to 170° C. and under from 1 to 500 bar thermally or in the presence of a heterogeneous catalyst.

9 Claims, No Drawings

PREPARATION OF MIXTURES OF 3-AMINOPROPIONITRILE AND ETHYLENE CYANOHYDRIN

The present invention relates to a novel process for preparing mixtures of aminopropionitrile and ethylene cyanohydrin by reacting bis(2-cyanoethyl) ether with ammonia in the presence of a heterogeneous catalyst at elevated temperatures.

It is known that in the preparation of 3-aminopropionitrile the monoaddition of ammonia onto acrylonitrile is always accompanied to a considerable extent by formation of the bisadduct bis(2-cyanoethyl)amine. U.S. Pat. No. 2,401,429 discloses that it is possible to isolate from acrylonitrile and liquid ammonia at room temperature after 2 days besides 11% 3-aminopropionitrile also 76% bis(2-cyanoethyl)amine as main product. Reaction of acrylonitrile under pressure with liquid ammonia at 90° C. gives 13% 3-aminopropionitrile (DE-A 598 185).

It is also known that the addition of protic solvents has an advantageous effect on the addition ammonia onto acrylonitrile. However, even when the ammonia/acrylonitrile/water ratio is 5–15:1:5–20, 3-aminopropionitrile is obtained besides bis (2-cyanoethyl)-amine in yields of only 57–80% (see, for example, U.S. Pat. No. 3,935,256, DE-A 24 36 651, U.S. Pat. No. 2 448 013, U.S. Pat. No. 2 019 903).

Ethylene cyanohydrin has been prepared commercially to date from ethylene oxide and hydrocyanic acid (U.S. Pat. No. 2 653 162).

However, the selectivity of the preparation of ethylene cyanohydrin from acrylonitrile/water is, like the preparation of 3-aminopropionitrile from acrylonitrile/ammonia, unsatisfactory. In the presence of bases, addition of water onto acrylonitrile leads, besides the formation of ethylene cyanohydrin, also to the bisadduct bis(2-cyanoethyl) ether as main product (eg. DE-A 11 89 975, U.S. Pat. No. 2,816,130, JP 83-71444).

Moreover, the conversion of the acrylonitrile in the reaction is incomplete, and there is formation of by-products (amides) which are difficult to remove. It is therefore necessary to work up aqueous acrylonitrile solutions to isolate ethylene cyanohydrin. The handling and the distillation of these acrylonitrile solutions give rise (apart from the additional costs caused by them) to problems since acrylonitrile is toxic and, moreover, prone to polymerization on distillation.

More suitable processes for preparing ethylene cyanohydrin therefore involve cleavage of the bis(2-cyanoethyl) ether with simultaneous binding of the acrylonitrile resulting from this.

In contrast to the synthesis of ethylene cyanohydrin, the specific synthesis of bis(2-cyanoethyl) ether in good yields by addition of one molecule of water onto two molecules of acrylonitrile has been described.

For example, EP-A 352 504 discloses the reaction of acrylonitrile with water in the presence of mineral bases or quaternary nitrogen bases.

JO-1090-160A describes the cleavage of the ether at 75–200° C. in the presence of bases such as tetraethylammonium acetate or alkali metal hydroxides to give ethylene cyanohydrin and acrylonitrile. This process does not solve all the problems of the circulation of free acrylonitrile.

According to DE-A 35 22 906, the ether can be reacted with methanolates to give ethylene cyanohydrin and 3-methoxypropionitrile. Although this process gives good yields, it inevitably results in large amounts of 3-methoxypropionitrile which has, however, only limited use.

The same applies to the 3-dialkylaminopropionitriles resulting from the preparation of ethylene cyanohydrin and 3-dialkylaminopropionitriles together described in EP-A 352 504.

It is an object of the present invention to remedy the abovementioned disadvantages.

We have found that this object is achieved by a novel process for preparing mixtures of 3-aminopropionitrile of the formula I $$H_2N-CH_2-CH_2-CN \qquad (I)$$

and ethylene cyanohydrin of the formula II $$HO-CH_2-CH_2-CN \qquad (II)$$

which comprises reacting bis(2-cyanoethyl) ether of the formula III $$NC-CH_2-CH_2-O-CH_2-CH_2-CN \qquad (III)$$

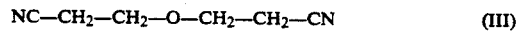

with ammonia at from 50 to 170° C. and under from 1 to 500 bar thermally or in the presence of a heterogeneous catalyst.

The present process can be carried out as follows: bis(2-cyanoethyl) ether III and ammonia can be reacted at from 50 to 170° C., preferably 90 to 150° C., particularly preferably 100 to 130° C., under from 1 to 500 bar, preferably 20 to 300 bar, particularly preferably 100 to 200 bar, thermally or, preferably, in the presence of a heterogeneous catalyst.

The cleavage can be carried out either batchwise or continuously. The batchwise reaction is expediently carried out under atmospheric pressure, whereas elevated pressure is preferred for the continuous process. The reaction is preferably carried out continuously under from 100 to 200 bar.

The residence time for the continuous reaction in a tubular reactor is from 0.5 min to 180 min, preferably 5 to 60 min, depending on the reactor volume.

The cleavage of bis(2-cyanoethyl) ether III to give ethylene cyanohydrin II and 3-aminopropionitrile I with ammonia in the presence of a heterogeneous catalyst comprises two reactions taking place in parallel: On the one hand the cleavage of the bis(2-cyanoethyl) ether III into ethylene cyanohydrin II and acrylonitrile and, on the other hand, the addition of ammonia onto acrylonitrile.

Particularly suitable heterogeneous catalysts are acidic and/or basic or amphoteric oxides of elements of groups IIa, IIIa and IVa, especially various modifications of $Al_2O_3$ and $SiO_2$ in the form of silica gel, kieselguhr or mixtures thereof; and of groups Ib to VIIB of the periodic table, of the lanthanides or mixtures thereof. Further advantageous catalysts which may be mentioned are titanium oxide, zirconium oxide, boron oxides, lanthanum oxide and tungsten oxides or mixtures thereof with aluminum oxide. Further catalysts for the process according to the invention are zeolites, phosphates and heteropolyacids. The abovementioned catalysts can also be impregnated with alkali metal oxides or mineral acids. Acidic or basic ion exchangers are likewise suitable as catalysts.

Ammonia and the bis(2-cyanoethyl) ether III are usually employed in the molar ratio from 1:1 to 100:1, preferably 10:1 to 50:1, particularly preferably 10:1 to 30:1. Ammonia can be used in liquid, anhydrous form or as aqueous solution.

Bis(2-cyanoethyl) ether can be employed in pure, distilled form or as solution of the ether in an inert solvent. Reaction mixtures which, besides bis(2-cyanoethyl) ether III in a concentration of from 10 to 90% by weight, contain water and acrylonitrile, with or without ethylene cyanohydrin II, are likewise suitable. The reaction can also be carried out in solvents which are inert under the reaction conditions.

Examples of suitable inert organic solvents are ethers such as dioxane, tetrahydrofuran or ethylene glycol dimethyl ether, or dimethylformamide.

The conversion of bis(2-cyanoethyl) ether is usually virtually quantitative.

The reaction mixture can be fractionated into its components in a conventional manner. Since it contains only small amounts of impurities, it can be further processed without further purification. For example, it is possible to hydrogenate the mixture of ethylene cyanohydrin and 3-aminopropionitrile resulting from the reaction to give the corresponding amines.

Ethylene cyanohydrin II and 3-aminopropionitrile I are important intermediates for the chemical industry. 3-Aminopropionitrile I is a suitable intermediate for preparing $\beta$-alanine (precursor for calcium pantothenate - DE-A 22 23 236), and of propylenediamine which is employed in pharmaceuticals, polyamides and wood preservatives (DE-A 32 48 326, DE-A 20 04 405).

Ethylene cyanohydrin II is widely used as intermediate for the preparation of dyes, crop protection agents, drugs and plastics.

EXAMPLES

Example 1

230 ml/h ammonia and 36 ml/h bis(2-cyanoethyl) ether (95% pure) were fed into an oil-heated tubular reactor with d volume of 100 ml packed with 50 ml of Al$_2$O$_3$/SiO$_2$ (80/20) (1-2 mm chips) and with inert quartz beads above and below (25 ml each) the Catalyst bed at 130° C. and under a total pressure of 200 bar. The discharge from the reactor has the following composition:
0.7% : water
37.8% : 3-aminopropionitrile
56.5% : ethylene cyanohydrin
2.9% : bis(2-cyanoethyl) ether
2.1% : bis(2-cyanoethyl)amine (5.5% of the weight of 3-aminopropionitrile).

Example 2

46 mi/h ammonia and 6.2 ml/h bis(2-cyanoethyl) ether (93% pure) were fed into an oil-heated tubular reactor with a volume of 100 ml packed with 50 ml of Al$_2$O$_3$/SiO$_2$ (80/20) (1-2 mm chips) and with inert quartz beads above and below (25 ml each) the catalyst bed at 110° C. and under a total pressure of 200 bar. The discharge from the reactor lids the following composition:
2.5% : water
41.2% : 3-aminopropionitrile
55.2% : ethylene cyanohydrin
1.0% : bis(2-cyanoethyl) ether
2.6% : bis(2-cyanoethyl)amine (6.3% of the weight of 3-aminopropionitrile).

Example 3

212 ml/h ammonia and 37 ml/h crude bis(2-cyanoethyl) ether (86% pure) were fed into an oil-heated tubular reactor with a volume of 100 ml packed with 50 ml of Al$_2$O$_3$/SiO$_2$ (80/20) (1-2 mm chips) and with inert quartz beads above and below (25 ml each) the catalyst bed at 150° C. and under a total pressure of 200 bar. The discharge from the reactor has the following composition:
0.5% : water
42.6% : 3-aminopropionitrile
54.0% : ethylene cyanohydrin
0.0% : bis(2-cyanoethyl) ether
2.7% : bis(2-cyanoethyl)amine (6.3% of the weight of 3-aminopropionitrile)
0.2% : acrylamide.

Example 4

260 ml/h ammonia and 48 ml/h crude bis(2-cyanoethyl) ether (60% pure, 11% by weight acrylonitrile, 12% by weight ethylene cyanohydrin, 12% by weight water, 3% by weight acrylamide) were fed into an oilheated tubular reactor with a volume of 100 ml packed with 50 ml of Al$_2$O$_3$/SiO$_2$ (80/20) (1-2 Mm chips) and with inert quartz beads above and below (25 ml each) the catalyst bed at 130° C. and under a total pressure of 200 bar. The discharge from the reactor has the following composition:
3.6% : water
48.3% : 3-aminopropionitrile
40.9% : ethylene cyanohydrin
2.2% : bis(2-cyanoethyl) ether
2.5% : bis(2-cyanoethyl)amine (5.1% of the weight of 3-aminopropionitrile)
0.4% : acrylamide.

Example 5

260 ml/h ammonia and 46 ml/h crude bis(2-cyanoethyl) ether (60% pure, 11% by weight acrylonitrile, 12% by weight ethylene cyanohydrin, 12% by weight water, 3% by weight acrylamide) were fed into an oilheated tubular reactor with a volume of 100 ml packed with 50 ml of TiO$_2$ (1-2 mm chips) and with inert quartz beads above and below (25 ml each) the catalyst bed at 110° C. and under a total pressure of 200 bar. The discharge from the reactor has the following composition:
6.1% : water
49.3% : 3-aminopropionitrile
36.7% : ethylene cyanohydrin
0.2% : bis(2-cyanoethyl) ether
3.2% : bis(2-cyanoethyl)amine (6.5% of the weight of 3-aminopropionitrile)
0.7% : acrylamide.

Example 6

124 ml/h amonia and 20 ml/h bis(2-cyanoethyl) ether (60% pure, 11% by weight acrylonitrile, 12% by weight ethylene cyanohydrin,, 12% by weight water, 3% by weight acrylamide) were fed into an oilheated tubular reactor with a volume of 100 ml packed with 50 ml of IRA ® 93 ion exchanger and with inert quartz beads above and below (25 ml each) the catalyst bed at 110° C. and under a total pressure of 200 bar. The discharge from the reactor has the following composition:

6.9% : water
44.9% : 3-aminopropionitrile
36.8% : ethylene cyanohydrin
4.2% : bis(2-cyanoethyl) ether
0.8% : bis(2-cyanoethyl)amine (1.8% of the weight of 3-aminopropionitrile)
0.2% : acryldmide.

Example 7

245 ml/h ammonia and 59 ml/h bis(2-cyanoethyl) ether (49% pure, 17% by weight acrylonitrile, 14% by weight ethylene cyanohydrin, 14% by weight water, 2% by weight acrylamide; the basic catalyst present from the bis(2-cyanoethyl) ether synthesis was neutralized with formic acid) were fed into an oil-heated tubular reactor with a volume of 100 ml packed with 50 ml of $Al_2O_3/SiO_2$ (80/20) (1-2 mm chips) and with inert quartz beads above and below (25 ml each) the catalyst bed at 110° C. and under a total pressure of 200 bar. The discharge from the reactor has the following composition:
7.3% : water
45.9% : 3-aminopropionitrile
36.1% : ethylene cyanohydrin
2.2% : bis(2-cyanoethyl) ether
2.5% : bis(2-cyanoethyl)amine (5.4% of the weight of 3-aminopropionitrile)
0.2% : acrylamide

Example 8

Without catalyst (thermal reaction)

250 ml/h ammonia and 41 ml/h bis(2-cyanoethyl) ether (40% pure) were fed into an oil-heated tubular reactor with a volume of 100 ml packed with 100 ml of quartz beads at 130° C. and under a total pressure of 200 bar. The discharge from the reactor has the following composition:
6.7% : water
30.7% : 3-aminopropionitrile
31.8% : ethylene cyanohydrin
22.2% : bis(2-cyanoethyl) ether
4.8% : bis(2-cyanoethyl)amine (15.6% of the weight of 3-aminopropionitrile)
1.2% : acrylamide

Example 9

238 ml/h ammonia and 45 ml/h bis(2-cyanoethyl) ether (90% pure) were fed into an oil-heated tubular reactor with a volume of 100 ml packed with 100 ml of quartz beads at 130° C. and under a total pressure of 200 bar. The discharge from the reactor has the following composition:
6.7% : water
19.6% : 3-aminopropionitrile
29.1% : ethylene cyanohydrin
39.3% : bis(2-cyanoethyl) ether
2.8% : bis(2-cyanoethyl)amine (14.3% of the weight of 3-aminopropionitrile)
1.2% : acrylamide

We claim:

1. A process for preparing mixtures of 3-aminopropionitrile of the formula I $$H_2N-CH_2-CH_2-CN \quad (I)$$

and ethylene cyanohydrin of the formula II $$HO-CH_2-CH_2-CN \quad (II)$$

which comprises reacting bis(2-cyanoethyl) ether of the formula III $$NC-CH_2-CH_2-O-CH_2-CH_2-CN \quad (III)$$

with ammonia at from 50 to 170° C. and under from 0.1 to 500 bar thermally or in the presence of a heterogeneous catalyst.

2. A process for preparing mixtures of 3-aminopropionitrile I and ethylene cyanohydrin II as claimed in claim 1, wherein the reaction is carried out at from 90 to 150° C.

3. A process for preparing mixtures of 3-aminopropionitrile I and ethylene cyanohydrin II as claimed in claim 1, wherein the reaction is carried out under from 1 to 500 bar.

4. A process for preparing mixtures of 3-aminopropionitrile I and ethylene cyanohydrin II as claimed in claim 1, wherein the reaction is carried out under from 20 to 300 bar.

5. A process for preparing mixtures of 3-aminopropionitrile I and ethylene cyanohydrin II as claimed in claim 1, wherein the reaction is carried out continuously.

6. A process for preparing mixtures of 3-aminopropionitrile I and ethylene cyanohydrin II as claimed in claim 1, wherein the reaction is carried out in tubular reactors.

7. A process for preparing mixtures of 3-aminopropionitrile I and ethylene cyanohydrin II as claimed in claim 1, wherein ammonia and bis(2-cyanoethyl) ether III are employed in the molar ratio of from 10:1 to 100:1.

8. A process for preparing mixtures of 3-aminopropionitrile I and ethylene cyanohydrin II as claimed in claim 1, wherein ammonia and bis(2-cyanoethyl) ether III are employed in the molar ratio of from 10:1 to 50:1.

9. A process for preparing mixtures of 3-aminopropionitrile I and ethylene cyanohydrin II as claimed in claim 1, wherein oxides of group IIa and/or IIIA and/or IVa or of groups Ib-VIIb of the periodic table of the elements or mixtures of the latter are used as heterogeneous catalysts.

* * * * *

UNITED STATES PATENT AND TRADEMARK OFFICE
CERTIFICATE OF CORRECTION

PATENT NO. : 5,268,499
DATED : Dec. 7, 1993
INVENTOR(S) : MERGER et al.

It is certified that error appears in the above-identified patent and that said Letters Patent is hereby corrected as shown below:

IN THE CLAIMS

Claim 7, column 6, line 44, "10:1" should read -- 1:1 --.

Signed and Sealed this

Third Day of May, 1994

BRUCE LEHMAN

Attest:

Attesting Officer

Commissioner of Patents and Trademarks